United States Patent [19]

Riegel et al.

[11] 4,346,069
[45] Aug. 24, 1982

[54] RECOVERY OF CHLORINE VALUES IN INTEGRATED PROCESS FOR OXYCHLORINATION AND COMBUSTION OF CHLORINATED HYDROCARBONS

[75] Inventors: Herbert Riegel, Maplewood; Chiung-Yuan Huang, Glen Ridge, both of N.J.

[73] Assignee: The Lummus Company, Bloomfield, N.J.

[21] Appl. No.: 228,462

[22] Filed: Jan. 26, 1981

[51] Int. Cl.³ .................. C01B 7/01; C07C 21/00
[52] U.S. Cl. ......................... 423/488; 423/240; 423/481; 570/203; 570/224; 570/225; 570/243; 570/244
[58] Field of Search ............... 423/240, 481, 488, 502, 423/507; 570/203, 224, 225, 243, 244

[56] References Cited

U.S. PATENT DOCUMENTS

| | | | |
|---|---|---|---|
| 3,816,599 | 6/1974 | Kafes | 423/488 |
| 3,950,443 | 4/1976 | Prahl | 570/243 X |
| 3,968,050 | 7/1976 | Riegel | 570/244 X |
| 3,968,200 | 7/1976 | Tsao | 423/488 |
| 4,036,776 | 7/1977 | Riegel et al. | 570/244 X |
| 4,073,871 | 2/1978 | Optiz | 423/481 |
| 4,119,705 | 10/1978 | Riegel et al. | 423/48 G |
| 4,133,786 | 9/1978 | Tsao | 570/244 |

Primary Examiner—Earl C. Thomas
Attorney, Agent, or Firm—Elliot M. Olstein; Louis E. Marn

[57] ABSTRACT

In an integrated process for oxychlorination and combustion of chlorinated hydrocarbons, chlorinated hydrocarbons is burned to recover chlorine values essentially as hydrogen chloride. Combustion effluent and off-gas from an oxychlorination reaction are simultaneously treated to recover anhydrous hydrogen chloride for use in the oxychlorination reaction. In accordance with one embodiment, off-gas from the oxychlorination is employed in the combustion, prior to hydrogen chloride recovery in order to utilize any oxygen values therein. The process has particular applicability to an oxychlorination reaction of the type wherein a molten salt containing the higher and lower valent chlorides of a multivalent metal is contacted with hydrogen chloride and oxygen to recover hydrogen chloride by enriching the higher valent metal chloride content of the molten salt.

3 Claims, 1 Drawing Figure

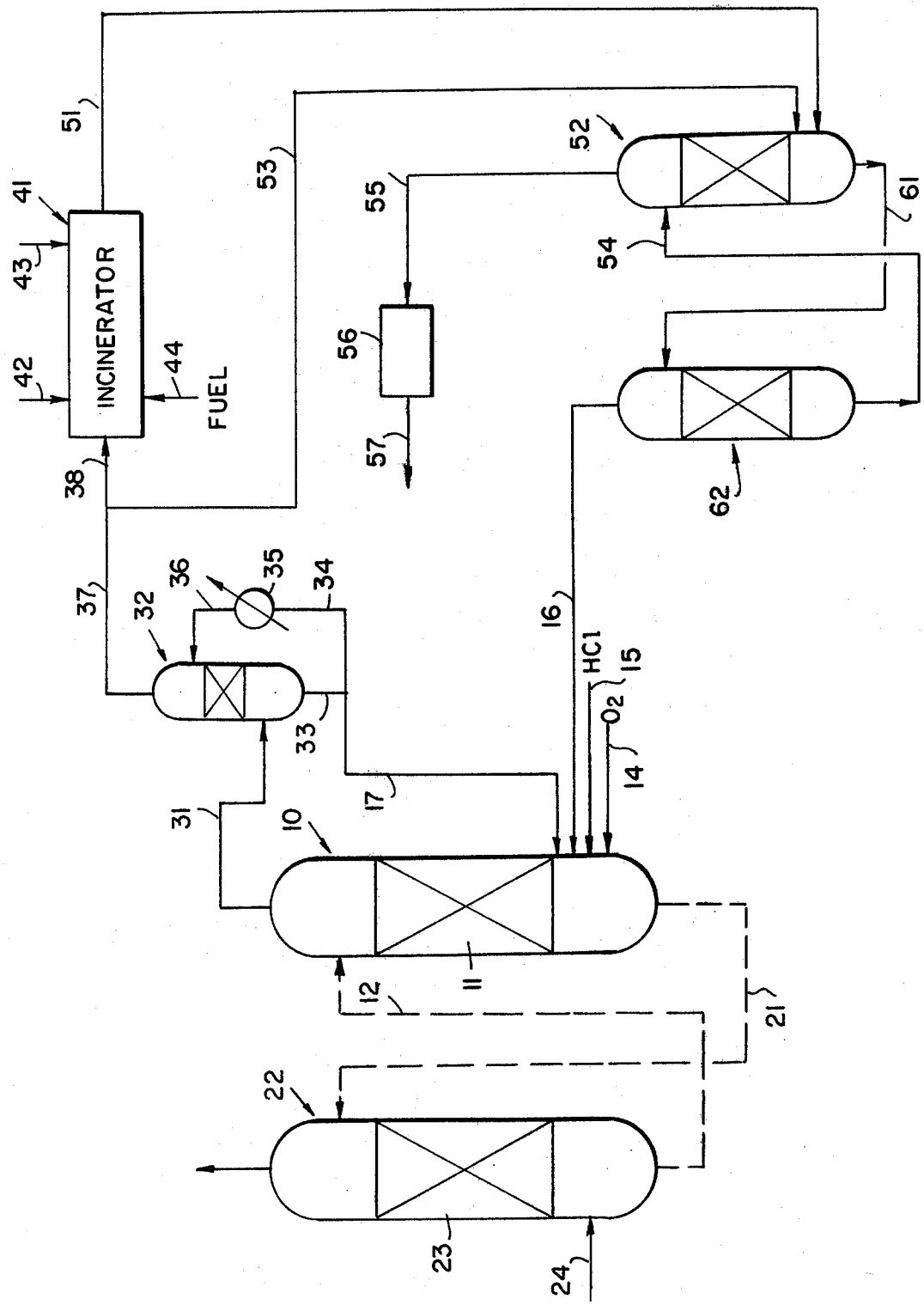

RECOVERY OF CHLORINE VALUES IN INTEGRATED PROCESS FOR OXYCHLORINATION AND COMBUSTION OF CHLORINATED HYDROCARBONS

This invention relates to recovery of chlorine values, and more particularly to recovery of chlorine values in an integrated process for oxychlorination and combustion of chlorinated hydrocarbons. Still more particularly, this invention relates to improving chlorine value recovery in a process wherein the oxychlorination involves contact of a molten salt containing the higher and lower valent chlorides of a multivalent metal with hydrogen chloride and oxygen, which is integrated with the combustion of chlorinated hydrocarbons.

Oxychlorination reactions using hydrogen chloride and oxygen are well known in the art. One type of oxychlorination reaction involves contacting a mixture of a multivalent metal chloride in both its higher and lower valent state, such as a mixture of cuprous and cupric chloride, either as an unsupported melt or supported on a suitable support, with hydrogen chloride and a molecular oxygen containing gas to increase the content of the higher valent metal chloride; e.g., cupric chloride, and in some cases also increase the oxide content of the mixture, generally as the oxychloride. Such mixture may then be employed for the chlorination of a hydrocarbon and/or partially chlorinated hydrocarbon, or for recovery of chlorine values therefrom as gaseous chlorine, or for other purposes.

Another type of oxychlorination reaction involves contacting hydrogen chloride and oxygen with the hydrocarbon or partially chlorinated hydrocarbon, generally in the presence of a suitable catalyst, to produce chlorinated hydrocarbons.

Processes for recovering chlorine values from a chlorinated hydrocarbon; in particular, a chlorinated hydrocarbon which cannot be economically converted to a desired chlorinated hydrocarbon, hereinafter sometimes referred to as a waste chlorinated hydrocarbon, are also known in the art. In general, the chlorinated hydrocarbon is burned to produce a gaseous effluent which includes hydrogen chloride, and in some cases, may further include chlorine, with the chlorine values present in the combustion effluent subsequently being recovered for economic utilization thereof. Such processes also depend upon economic recovery of hydrogen chloride from the gas.

U.S. Pat. No. 3,968,200 discloses a process for recovery of chlorine values in a process which integrates combustion of chlorinated hydrocarbons with an oxychlorination reaction. In accordance with such patent, waste chlorinated hydrocarbons are burned to produce a gaseous effluent containing hydrogen chloride and chlorine, with the gaseous effluent then being contacted with a molten salt to recover chlorine values therefrom. Hydrogen chloride present in the effluent from the molten salt contacting step is then recovered by a series of quenching steps.

U.S. Pat. No. 3,816,599 discloses a process for recovering essentially anhydrous hydrogen chloride from an oxychlorination effluent for recycle thereto by the use of high pressure and low pressure towers.

In accordance with the present invention there is provided a process wherein chlorinated hydrocarbon combustion is integrated with an oxychlorination reaction, and which provides for effective recovery of chlorine values. In accordance with the present invention, the chlorinated hydrocarbon is burned to produce a combustion effluent which contains the chlorine values present in the chlorinated hydrocarbon as essentially hydrogen chloride. The gaseous combustion effluent, which contains hydrogen chloride, and an off-gas from an oxychlorination reaction are simultaneously treated to recover anhydrous hydrogen chloride for use in the oxychlorination reaction.

Off-gas from the oxychlorination reaction, which generally contains water vapor and some hydrogen chloride, and which may further contain some oxygen, depending upon the oxygen content thereof, may be initially introduced into the chlorinated hydrocarbon combustion, prior to recovery of anhydrous hydrogen chloride in order to employ any oxygen values therein for combusting of the chlorinated hydrocarbon. In the alternative, the off-gas may be passed to the anhydrous hydrogen chloride recovery, without prior utilization in the combustion. It is to be understood that a portion of such off-gas may be introduced into the combustion and a further portion passed directly to the hydrogen chloride recovery. In some cases, particularly where the oxychlorination reaction is one employing a molten salt, as hereinafter described, the off-gas is cooled to condense some aqueous hydrogen chloride and thereby recover any salt entrained in the off-gas, with such condensed portion being returned to the oxychlorination reaction. Subsequent to such cooling to recover entrained salt in a condensed portion, the off-gas may be employed in the combustion and/or anhydrous hydrogen chloride recovery, as hereinabove described.

By proceeding in accordance with the present invention, it is possible to recover chlorine values from the chlorinated hydrocarbon combustion effluent in the form of essentially anhydrous hydrogen chloride, which thereby reduces the total flow to the oxychlorination reaction. Furthermore, it is not necessary to compress the oxygen to the combustion step in that the combustion effluent gas is not directly introduced into the oxychlorination reaction, which may be operated at an elevated pressure. Furthermore, in accordance with the embodiment wherein the off-gas from the oxychlorination is employed in the combustion, oxygen values present in such off-gas may be effectively utilized in the combustion.

The oxychlorination reactions to which the present invention are applicable are of several types and include: (1) reaction between molecular oxygen, hydrogen chloride and a salt mixture of the higher and lower valent forms of a multivalent metal chloride to enrich the higher valent metal chloride content of the mixture, and in some cases, depending upon the amount of of oxygen employed, and depending upon the desired applications, the salt may be further enriched in oxygen, generally as the oxychloride; (2) reaction between molecular oxygen, hydrogen chloride and the hydrocarbon or a partially chlorinated hydrocarbon, generally a lower (1 to 4 carbon atoms) aliphatic hydrocarbon or partially chlorinated lower aliphatic hydrocarbon to produce a chlorinated hydrocarbon; (3) reaction between hydrogen chloride and oxygen to produce chlorine (generally referred to as a Deacon reaction, but for the purposes of this invention this reaction is considered an oxychlorination); (4) reaction between an oxychloride of the multivalent metal and hydrogen chloride to produce the higher valent metal chloride; and (5) reaction between an oxychloride of the multivalent metal, hydrogen chloride and a hydrocarbon or partially chlorinated hydrocarbon to produce a chlorinated hydrocarbon.

The present invention has particular applicability to an oxychlorination reaction of the type wherein molecular oxygen, hydrogen chloride and a salt mixture of the higher and lower valent forms of a multivalent metal chloride are reacted to enrich the higher valent metal chloride content of the mixture, with as hereinabove noted, the reaction sometimes being effected in order to also increase the oxygen content of the mixture, generally as the oxychloride. In particular, the salt mixture of the higher and lower valent forms of a multivalent chloride is employed as an unsupported molten salt mixture. Such molten salts are known in the art, and no further details in this respect are deemed necessary for a complete understanding of the invention. As generally known in the art, such multivalent metals have more than one positive valent state, and are generally the chlorides of iron, manganese, copper, cobalt or chromium, preferably copper. Such molten salt mixtures also generally include a melting point depressant, which is preferably an alkali metal chloride, or which may be other metal chlorides.

The invention will be further described with respect to an embodiment thereof illustrated in the accompanying drawing, wherein:

The drawing is a simplified schematic flow diagram of an embodiment of the invention.

It is to be understood, however, that the scope of the invention is not to be limited to such embodiment.

Referring now to the drawing, there is shown a molten salt oxychlorination reactor, schematically generally indicated as 10, which includes suitable means, such as packing, schematically designated as 11, for increasing gas liquid contact. The molten salt oxychlorination reactor is designed and operated, as known in the art, for recovering chlorine values by enriching the higher valent metal chloride content of the molten salt mixture. As particularly described, the molten salt mixture, which contains cuprous and cupric chloride, and which further includes, as a melting point depressant, potassium chloride is introduced into the reactor through line 12. It is to be understood, however, that other molten salt mixtures, as known in the art, may also be used although the salt is preferably a molten salt mixture which contains cuprous and cupric chloride. The oxidation reactor 10 is further provided with oxygen through line 14. The reactor 10 may be further provided with hydrogen chloride, in line 15, with such hydrogen chloride being either a recycle stream from another portion of the plant or fresh feed hydrogen chloride. The reactor 10 is further provided with recovered hydrogen chloride, as hereinafter described, with such recovered hydrogen chloride being either derived from the combustion of a chlorinated hydrocarbon(s) and/or hydrogen chloride recovered from the effluent withdrawn from reactor 10, as hereinafter described. Such recovered hydrogen chloride is provided as anhydrous hydrogen chloride in line 16 and may also be provided as aqueous hydrogen chloride, which includes entrained salt, provided through line 17.

The reactor 10 is operated in a manner such that as a result of the countercurrent contact between the molten salt introduced through line 12, the oxygen introduced through line 14 and hydrogen chloride introduced into reactor 10 through one or more of lines 15, 16, and 17, hydrogen chloride is recovered by enriching the higher valent metal chloride content of the salt; namely cupric chloride. In addition, if required, the salt may also be oxidized to provide the salt with an oxygen content, namely as copper oxychloride. Chlorine may also be introduced into reactor 10 with such chlorine being recovered in the salt as cupric chloride.

The oxidation reactor 10 is generally operated at a pressure of from about 1 atm. to about 20 atms., preferably at a pressure of from about 3 atms. to about 6 atms. The salt inlet temperature to the oxidation reactor 10 is generally from about 750° F. to about 950° F., preferably from about 770° F. to about 840° F.

The molten salt, having an enriched content of cupric chloride, and which may further include oxygen, as the oxychloride, is withdrawn from reactor 10 through line 21 for introduction into a further reactor, schematically generally indicated as 22, which also includes packing 23 for increasing gas liquid contact. The reactor 22 may utilize the molten salt, having an enriched cupric chloride content, in any one of a wide variety of ways, as known in the art. Thus, for example, chlorine values may be recovered from the molten salt, as gaseous chlorine. Thus, for example, such a process is described in U.S. Pat. No. 4,119,705. In addition, chlorine can be recovered from the salt for use in the production of chlorinated hydrocarbons, as described, for example, in U.S. Application Ser. No. 879,802 filed on Feb. 21, 1978, or U.S. Application Ser. No. 002,687, filed on Jan. 11, 1979. In such cases, a stripping gas may be introduced into reactor 22 through line 24.

The reactor 22 may also be employed for the production of chlorinated hydrocarbons, as known in the art, in which case hydrocarbon feed and hydrogen chloride and/or chlorine are also introduced into reactor 22 through line 24. Such a process is known in the art, and no further details in this respect are deemed necessary for a complete understanding of the present invention.

The molten salt withdrawn from reactor 22 through line 12 is employed in reactor 10, as hereinabove described.

A gas, containing unreacted hydrogen chloride, water vapor, any components introduced with the hydrogen chloride and oxygen, as well as any components introduced with the oxygen; for example, nitrogen when air is employed, as well as entrained salt, is withdrawn from reactor 10 through line 31 for further treatment to separate entrained salt therefrom. As particularly shown, the gas in line 31 is introduced into a quench tower, schematically generally indicated as 32, wherein the gas is contacted with a quench liquid introduced into tower 32 through line 33 in order to cool the gas by direct contact quench cooling to thereby condense aqueous hydrogen chloride, which contains entrained salt. The cooling in tower 32 is preferably effected to minimize the condensation of aqueous hydrogen chloride in that the main purpose for the cooling step is to separate entrained salt.

Condensate, containing entrained salt is withdrawn from tower 32 through line 33, and a portion thereof is circulated through line 34, including a suitable cooler 35 for introduction as quench liquid through line 36.

The remaining portion is recycled to reactor 10 through line 17.

The remaining gas, essentially free of entrained salt, is withdrawn from tower 32 through line 37.

The primary purpose for the quenching in line 32 is for removal of entrained salt, and it is to be understood, that if the entrained salt would not present a problem in subsequent processing steps, the quench tower 32 could be eliminated. Alternatively, other means for separating entrained salt from the effluent in line 31 may be employed. It is also to be understood that if the oxychlorination reaction does not employ a molten salt, whereby the oxychlorination off-gas does not include entrained salt, the quench cooling in tower 32 may be eliminated.

The oxychlorination off-gas in line 37, which is now free of entrained salt may be further treated in accordance with alternative procedures as shown with reference to the drawing; i.e., the off-gas may be introduced directly into the hydrogen chloride recovery step in conjunction with incineration effluent and/or the off-gas may be introduced into the chlorinated hydrocarbon combustion zone. If the off-gas in line 37 contains sufficient oxygen values that introduction thereof into the chlorinated hydrocarbon combustion step is beneficial, then the off-gas, in line 38 is introduced into a chlorinated hydrocarbon combustion zone, schematically generally indicated as 41. Such off-gas in line 38 contains some oxygen, some hydrogen chloride and inerts, such as nitrogen, which may have been introduced with the oxygen. The chlorinated hydrocarbon incineration or combustion zone 41 is provided with chlorinated hydrocarbons to be burned in line 42, oxygen, if required in line 43, which may be provided as air or as oxygen, and fuel, if required in line 44. The incineration or combustion zone 41 is operated at temperatures and pressures to burn the chlorinated hydrocarbon so as to recover the chlorine values essentially as hydrogen chloride. Thus, in accordance with the preferred operation, the combustion effluent should contain no more than about 100 ppm of chlorine. In general, the incineration zone 41 is operated at an outlet temperature in the order of from 1900° to 2300° F., in order to insure that the chlorine values are recovered essentially as hydrogen chloride. As known in the art, the chlorinated hydrocarbons which are introduced into the combustion zone 41 are generally heavier chlorinated hydrocarbons which cannot be economically reconverted to desired chlorinated product. Such heavy chlorinated hydrocarbons and the combustion thereof are known in the art, and as a result, no further details thereof are deemed necessary for a complete understanding of the present invention.

In general, the outlet of the incinerator is provided with a waste heat boiler for steam generation.

A combustion effluent is withdrawn from the combustion zone 41 through line 51, and such combustion effluent may also include the off-gas from the oxychlorination, if introduced into the incineration zone 41 through line 38. The effluent in line 51 contains hydrogen chloride derived from combusting the chlorinated hydrocarbons introduced into the combustion zone, as well as any hydrogen chloride present in the oxychlorination off-gas introduced into the combustion zone 41 through line 38. In addition, as hereinabove described, the combustion effluent in line 51 contains less than 100 ppm of chlorine.

The gas in line 51 is then treated to recover anhydrous hydrogen chloride therefrom with such recovery, as being particularly shown being accomplished by the use of first and second towers 52 and 62 operated at temperatures and pressures to recover anhydrous hydrogen chloride as overhead from tower 62 and water, essentially free of hydrogen chloride, as overhead from tower 52. The tower 52 functions basically as an absorption tower to recover hydrogen chloride present in the gas by absorption, with aqueous hydrogen chloride functioning as an absorption liquid, and tower 62 functions as a stripping tower to strip anhydrous hydrogen chloride from the enriched aqueous hydrogen chloride absorption liquid, with the lean aqueous hydrogen chloride absorption liquid being recycled to tower 52. The gas in line 51 is introduced into the bottom of tower 52. In addition, any oxychlorination off-gas in line 37, which was not introduced into the combustion zone 41 through line 38, is introduced into the tower 52 through line 53. The tower 52 is provided with an aqueous hydrogen chloride provided through line 54, with such aqueous hydrogen chloride absorbing the hydrogen chloride present in the gas.

The tower 52 is generally operated at a temperature of from 225° F. to 250° F., and at a pressure in the order of from 15 to 20 psia. to recover about a 21%, by weight, aqueous hydrogen chloride solution.

Unabsorbed gas is withdrawn from tower 52 through line 55, and such gas may contain inerts, such as nitrogen, which are present in the effluent from the oxychlorination reactor 10 and incinerator 41, and such gas is essentially free of hydrogen chloride. The gas in line 55 may be suitably treated, for example in zone 56 with aqueous alkali in order to remove any remaining hydrogen chloride. The remaining gas is recovered from zone 56 in line 57, and may then be purged from the system.

Aqueous hydrogen chloride rich absorption liquid is withdrawn from tower 52 through line 61 and introduced into a tower 62, which is operated to recover essentially anhydrous hydrogen chloride as overhead. In order to change the azeotropic composition, tower 62 is operated at a pressure higher than tower 22. The tower 62 is operated, for example, at a temperature in the order of from 300° F. to 350° F., and at a pressure in the order of from 65 to 115 psia. The tower 62 may also be provided, if required, with a stripping gas to enhance stripping of anhydrous hydrogen chloride. The stripped anhydrous hydrogen chloride is withdrawn from tower 62 through line 16 for introduction into the oxychlorination reactor 10.

Aqueous hydrogen chloride is withdrawn from tower 62 through line 54 for introduction into tower 52, with such aqueous hydrogen chloride having a reduced hydrogen chloride concentration.

Thus, in accordance with the disclosed embodiment, chlorine values are effectively recovered from a waste chlorinated hydrocarbon, as hydrogen chloride, such hydrogen chloride is recovered by the use of a molten salt for subsequent recovery as chlorine and/or utilization in a process requiring chlorine values, without the necessity of increasing the total flow requirements to the oxychlorination reactor 10. In addition, it is not necessary to compress oxygen gas employed in the incineration. Furthermore, it is possible to recover oxygen values present in the effluent from the oxychlorination reactor 10 by utilization thereof in the incinerator 41. Furthermore, hydrogen chloride present in the oxychlorination reaction effluent, and hydrogen chloride generated in the incinerator are simultaneously recovered for subsequent utilization in the oxychlorination reaction.

Although the invention has been described with respect to a particular embodiment thereof, it is to be understood that the scope of the invention is not to be limited thereby. Thus, for example, the oxychlorination reactor 10 could be a reactor for effecting oxychlorination other than by use of a molten salt, as particularly described. In such case, it may be possible to eliminate the initial quenching of the oxychlorination effluent, whereby the effluent may be employed directly in the incineration and/or hydrogen chloride recovery step.

As a further alternative, anhydrous hydrogen chloride could be recovered other than by the use of towers operated at different pressures; e.g., by the use of an azeotrope breaker such as calcium chloride.

As should be apparent, the present invention has applicability to a wide variety of processes which employ molten salts in which the molten salt is oxidized (oxychlorinated) by contacting the molten salt with oxygen and hydrogen chloride, and wherein chlorine values are recovered from a chlorinated organic compound, as hydrogen chloride, by incineration, with such hydrogen chloride being subsequently utilized for the production of valuable products through the use of a molten salt. In most cases, the waste chlorinated hydrocarbons which are burned in the incinerator are those which are produced, as byproducts, in the process which utilizes the molten salt; however, it is to be understood that chlorinated organics from extraneous sources may also be employed in such incinerator for recovery of chlorine values therefrom.

The present invention is particularly advantageous in that it permits effective recovery of hydrogen chloride, without the necessity of passing large volumes of gas through the oxychlorination (oxidation) reactor. In addition, oxygen values which may be present in the effluent from the oxychlorination reactor are effectively utilized in the process. Furthermore, such a result can be accomplished without the necessity of compressing the oxygen feed to the incinertion.

In addition, by passing the oxychlorination effluent through the incinerator, any hydrocarbons present in the effluent are combusted thereby providing a purer purge gas.

Numerous modifications and variations of the present invention are possible in light of the above teachings and, therefore, within the scope of the appended claims, the invention may be practised otherwise than as particularly described.

We claim:

1. A process for integrating an oxychlorination reaction with combustion of chlorinated hydrocarbons, comprising:

recovering a gas containing hydrogen chloride and water vapor from an oxychlorination reaction;

combusting a chlorinated organic compound to produce a combustion gas including chlorine values from the chlorinated organic compound essentially as hydrogen chloride;

simultaneously treating effluent from the combusting and said gas from the oxychlorination reaction to recover anhydrous hydrogen chloride therefrom; and employing recovered anhydrous hydrogen chloride in the oxychlorination reaction.

2. The process of claim 1 wherein such gas from the oxychlorination is employed in said combusting.

3. The process of claim 2 wherein anhydrous hydrogen chloride is recovered from combined combustion and oxychlorination gas in a two tower recovery zone, wherein water essentially free of hydrogen chloride is recovered as overhead from a first tower, essentially anhydrous hydrogen chloride is recovered from a second tower, said second tower being operated at a pressure higher than the first tower, and bottoms from the second tower being introduced into the first tower and bottoms from the first tower being introduced into the second tower.

* * * * *